United States Patent
Knox et al.

(10) Patent No.: US 7,924,971 B2
(45) Date of Patent: Apr. 12, 2011

(54) RADIOGRAPHIC APPARATUS

(75) Inventors: Christopher Knox, East Grinstead (GB); Andrew Long, Leatherhead (GB); Kevin Brown, Horsham (GB)

(73) Assignee: Elekta AB (Publ) (SE)

( * ) Notice: Subject to any disclaimer, the term of this patent is extended or adjusted under 35 U.S.C. 154(b) by 99 days.

(21) Appl. No.: 12/445,203

(22) PCT Filed: Oct. 11, 2006

(86) PCT No.: PCT/EP2006/009801
§ 371 (c)(1),
(2), (4) Date: Apr. 10, 2009

(87) PCT Pub. No.: WO2008/043378
PCT Pub. Date: Apr. 17, 2008

(65) Prior Publication Data
US 2010/0104070 A1    Apr. 29, 2010

(51) Int. Cl.
*A61B 6/00*      (2006.01)
(52) U.S. Cl. ............................ 378/8; 378/95
(58) Field of Classification Search ................ 378/4–20, 378/62, 65, 95
See application file for complete search history.

(56) References Cited

U.S. PATENT DOCUMENTS

| 2004/0081269 | A1 | 4/2004 | Pan et al. |
| 2004/0218719 | A1* | 11/2004 | Brown et al. ................... 378/95 |
| 2005/0113702 | A1 | 5/2005 | Salla et al. |
| 2005/0185758 | A1 | 8/2005 | Bruder et al. |

FOREIGN PATENT DOCUMENTS

| EP | 1 333 248 A | 8/2003 |
| EP | 1 350 468 A | 10/2003 |
| EP | 1 542 165 A | 6/2005 |

OTHER PUBLICATIONS

PCT International Search Report, Jul. 9, 2007.

* cited by examiner

*Primary Examiner* — Courtney Thomas
(74) *Attorney, Agent, or Firm* — Westman, Champlin & Kelly

(57) ABSTRACT

For Respiration Correlated Cone Beam CT scanning, we have observed that improvements in the frame rate are in fact undesirable. We therefore propose a radiographic apparatus comprising a beam of radiation and a detector therefor, adapted to obtain a two dimensional image of the beam after passing through a cyclically varying object to be investigated, a processor adapted to review the images and select images at like points in the cycle, and a control means for the beam of radiation adapted to activate the beam periodically. The control means can activate the beam at a frequency of between 0.5 and 5 Hertz, more preferably between 1 and 3 Hertz, which corresponds (roughly) to a frequency that is between 6 and 10 times the frequency of the cyclical variation. It will assist if the selected point of the cycle is an extremity thereof, as the rate of change in these areas is at a minimum. Thus, slight mismatches between the two cycles will then have only a small effect. Typically, the object will be a patient and the cyclical variation will be the patient's breathing cycle.

18 Claims, 3 Drawing Sheets

RADIOGRAPHIC APPARATUS

CROSS-REFERENCE TO RELATED APPLICATION

This Application is a Section 371 National Stage Application of International Application No PCT/EP2006/009801, filed Oct. 11, 2006 and published as WO 2008/043378 A1 on Apr. 17, 2008, the content of which is hereby incorporated by reference in its entirety.

FIELD OF THE INVENTION

The present invention relates to radiographic apparatus, including such apparatus when operating alone or in conjunction (for example integrated with) radiotherapeutic apparatus.

BACKGROUND ART

Cone beam computed tomography (CBCT) scanners are well known and produce useful images of the interior structure of patients. They are invaluable as a diagnostic tool, and can also be used in conjunction with radiotherapeutic apparatus to produce realtime positional verification of organ location and even realtime guidance of the therapeutic radiation.

Such scanning does however meet with difficulties if the patient is not still. The three-dimensional tomograph is computed from a number of two-dimensional images, and the assumption must be made that the images are of an identical structure. If the patient (or parts of the patient) have moved between images then this results in degradation of the tomography and/or image artifacts. Such movement is of course inevitable, in the form of respiration and cardiac cycles.

Generally, improvements in the apparatus that allow a higher frame rate are regarded as desirable. These allow more images to be collected in a shorter time, resulting in an improved three dimensional tomography and/or reduced time demands on the patient.

To overcome the issue of respiration artifacts, we have proposed CBCT scanning that is correlated with the respiration cycle. This can be done either by detecting the respiration cycle and gating the scanner accordingly, or by scanning the patient and ascertaining the cyclical phase of a specific image from the image content. WO2004/06464 and WO2004/066211 describe such systems and a suitable algorithm for determining the phase of a specific image. This allows images of the "wrong" phase to be discarded prior to computation. Such respiration correlated CBCT (RCCBCT) allows good quality images of structures close to the lungs and/or diaphragm to be obtained.

SUMMARY OF THE INVENTION

For RCCBCT, we have observed that improvements in the frame rate are in fact undesirable. Instead of obtaining more images (or the same number more quickly), a higher frame rate simply results in a greater number of images being discarded by the selection algorithm. This means that there are no improvements in image quality or in the time required for acquisition, and the patient is exposed to a greater radiation dose without any corresponding benefit.

We therefore propose a radiographic apparatus comprising a beam of radiation and a detector therefor, adapted to obtain a two dimensional image of the beam after passing through a cyclically varying object to be investigated, a processor adapted to review the images and select images at like points in the cycle, and a control means for the beam of radiation adapted to activate the beam periodically.

The control means can activate the beam at a frequency of between 0.5 and 5 Hertz, more preferably between 1 and 3 Hertz. This ideally corresponds (roughly) to a frequency that is between 6 and 10 times the frequency of the cyclical variation.

It will assist if the selected point of the cycle is an extremity thereof, as the rate of change in these areas is at a minimum. Thus, slight mismatches between the two cycles will then have only a small effect.

Typically, the object will be a patient and the cyclical variation will be the patient's breathing cycle.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
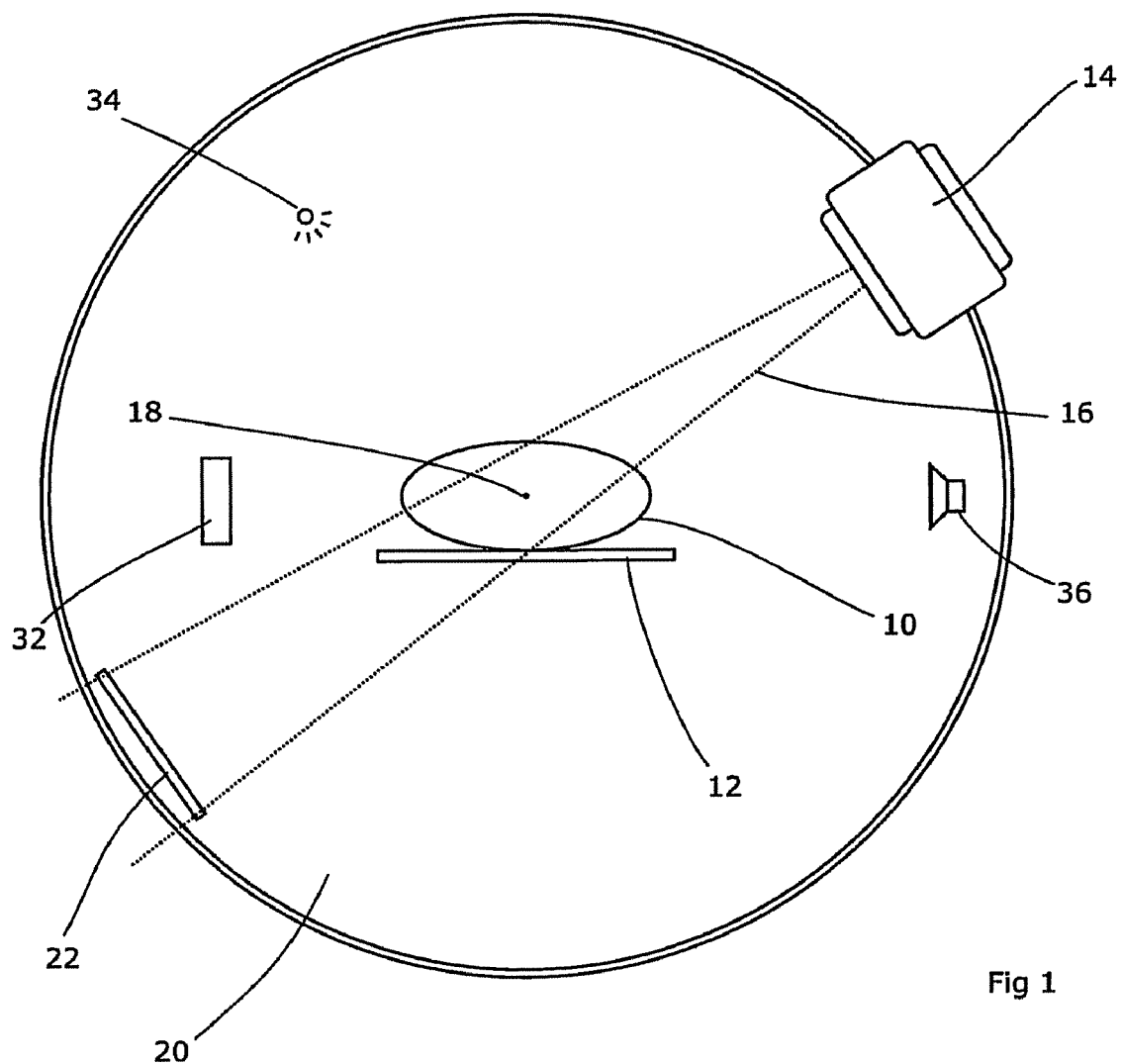
FIG. 1 is a view of a cone beam CT scanner according to the present invention, viewed along the axis of rotation thereof.

FIG. 1 shows a cone beam CT scanner. A patient 10 is supported on a couch 12 which may be of any suitable design. Couches typically allow the elevation and longitudinal position of the patient to be adjusted, and this may be provided for as desired.

An x-ray source 14 is arranged to project a wide beam 16 of radiation generally directed towards the isocentre 18 of the patient. The source 14 is rotatable around the isocentre 18 on a rotational support 20. The support can, for example, be in the form of a ring or annulus around the patient 10 and couch 12 in which the source is mounted, or it can be a C-arm, or any suitable support allowing the source to rotate, or any combination thereof.

A two-dimensional flat-panel detector 22 is also mounted on the support 20, opposite the source 14 and arranged to rotate in synchronism therewith. If the support includes a C-arm then this can be achieved by mounting the detector on the opposite arm.

Thus, radiation emitted by the source 14 is partially absorbed by the patient and the attenuated signal is detected by the flat panel detector 22. The source 14 and detector 22 are then indexed rotationally and a fresh image obtained. This is repeated until sufficient images are acquired to reconstruct the volume data, typically one complete rotation.

Figure 2:
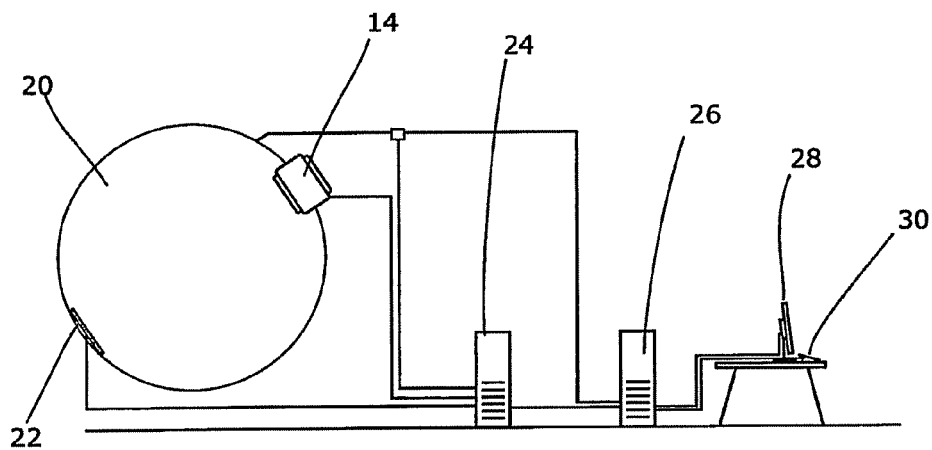
FIG. 2 is a schematic view of the system incorporating such a scanner.

FIG. 2 shows the system as a whole. The scanner of FIG. 1 is shown, together with cables linking the source 14, detector 22 and rotational support 20 to a plurality of computing means 24, 26 which process the data generated including the images, source intensity (etc), and rotational support position. Data is output via any suitable means, depicted generally as a monitor 28 but not limited thereto, and the system is controlled by any suitable input means, again depicted generally as a keyboard 30 but likewise not especially limited thereto.

As mentioned above, we have found that there are artifacts in the reconstructed volume data of cone beam CT systems, which we have traced to patient breathing movements. To overcome or alleviate these, respiration correlation techniques are applied to the acquired projection images by the computing means 24, 26.

To assist in this process, a breath control system is provided at 32 to monitor the phase of the patients breathing while the projection images are acquired. On completion of the acquisition, projection images that have comparable breathing phases can be selected from the complete set, and these are used to reconstruct the volume data using cone beam CT techniques. As a result, any phase or range of phases can be selected and therefore the effect of breathing can be studied if desired.

As an alternative to the breath control system, it is possible to use a feature in the projection image(s) to determine the breathing phase, such as the position of the patient's diaphragm. This can then be used to select the relevant images to be used in the projection process.

An alert system including a light 34 and a buzzer 36 is provided, to prompt the patient visually and audibly in order to ensure a regular amplitude and pattern of breathing. Other alerts could of course be employed, such as other forms of visible prompts including (for example) movable devices, and other forms of audible prompts including (for example) speakers, percussive devices or any other form of controllable sound generation apparatus.

As a further alternative to the breath control system, the images can be analysed to ascertain their phase and the appropriate images selected for use. An example of such analysis is set out in WO2004/066211, the content of which is hereby incorporated by reference. The reader is alerted that the disclosure of WO2004/066211 is considered relevant to this application and may be used as a source of amendments to this application if necessary.

Figure 3:
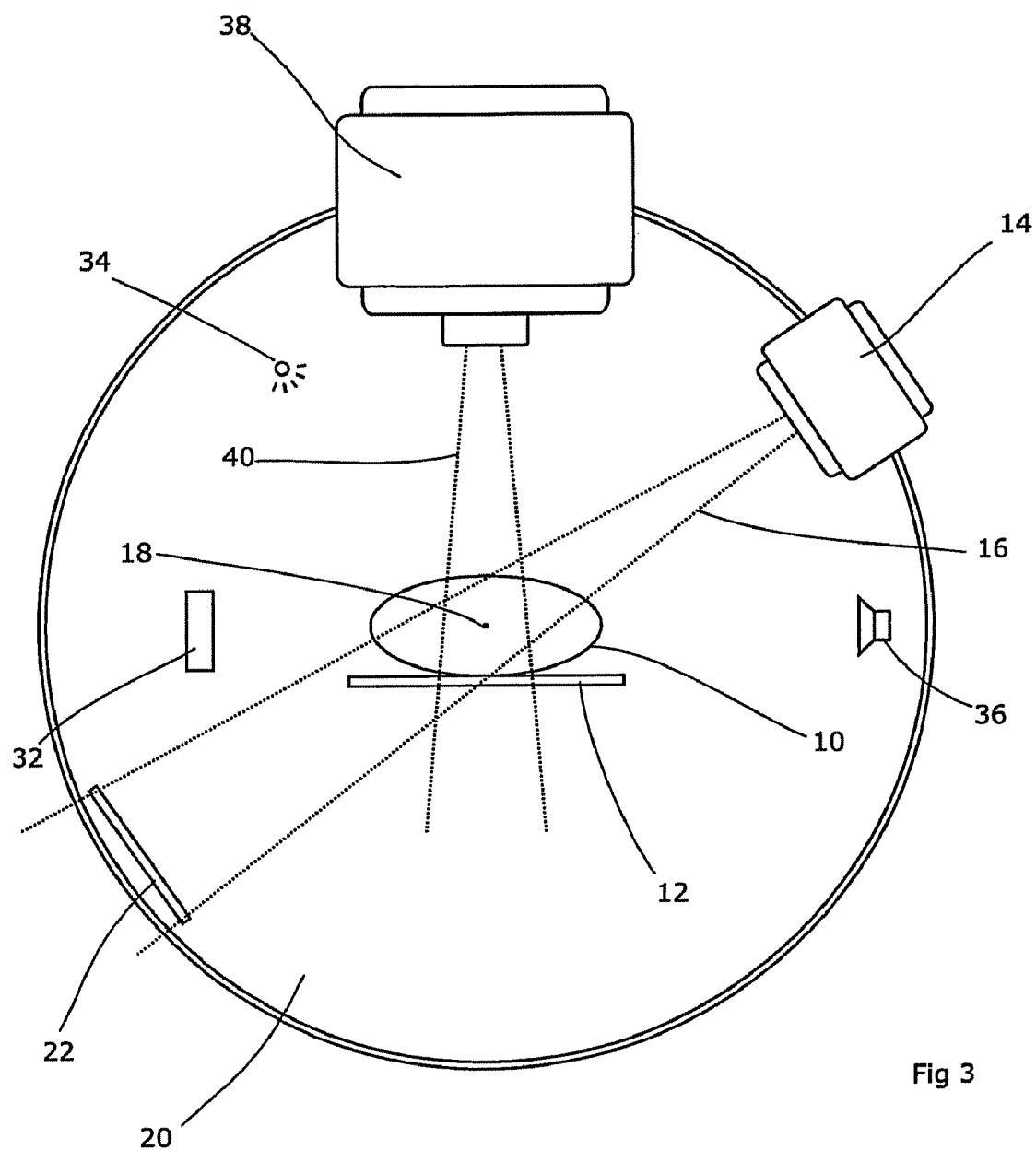
FIG. 3 shows a treatment apparatus including the scanner of the present invention.

FIG. 3 shows a system including a therapeutic source of radiation 38 arranged to emit a suitably collimated beam of therapeutic radiation 40. This allows simultaneous scanning and treatment. If the radiation from source 14 continues during the treatment, the output of the radiographic apparatus can be used to control delivery of therapeutic radiation from the source 38, dependent on the patient's breathing cycle. This ensures that the tumour is in the correct position when the radiation is delivered.

Figure 4:
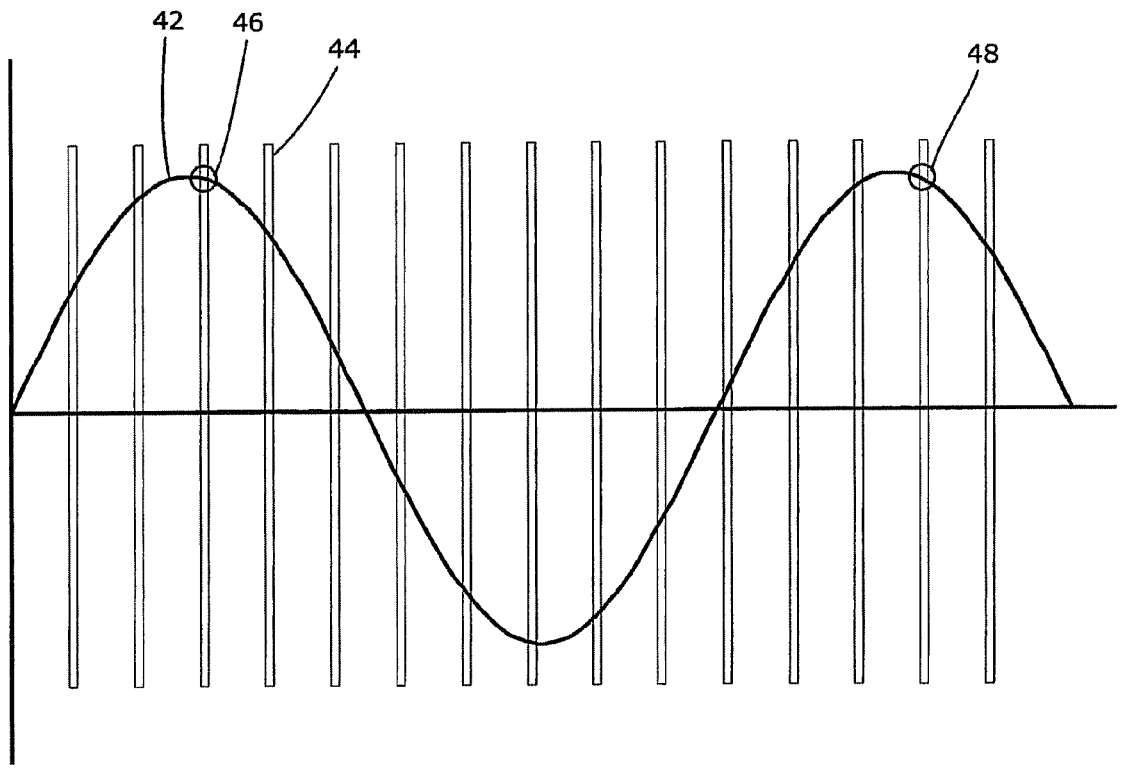
FIG. 4 shows the effect of phasing the radiation delivery according to the present invention.

Such monitoring does of course mean that many images are discarded. To limit the dose applied to the patient, therefore, the source 14 is pulsed as shown in FIG. 4. The typical breathing cycle 42 has a period of about 4 seconds, i.e. a frequency of about 0.25 Hz. A pulse rate of 2 Hz therefore produces about 8 scans 44 per breathing cycle. If we (arbitrarily) choose a particular point in the breathing cycle, it can be seen that an image 46, 48 is obtained close to that point in each cycle. This applies even though (as shown in FIG. 4) the breathing cycle is only approximately 0.25 Hz and therefore the pulse rate is not an exact multiple of the breathing cycle. Selection of a point in the breathing cycle corresponding to one of the limits thereof will assist since the rate of change at this point is less.

It will of course be understood that many variations may be made to the above-described embodiments without departing from the scope of the present invention.

The invention claimed is:

1. A radiographic apparatus comprising a source of a beam of radiation and a detector therefor, adapted to obtain a two dimensional image of the beam after passing through a cyclically varying object to be investigated, a processor adapted to review a plurality of the images, select images from the plurality of images at like points in the cycle in order to form a subset of images and reconstruct a volume image of the object from said subset, and a control means for the source of the beam of radiation adapted to pulse the beam periodically.

2. The radiographic apparatus according to claim 1 in which the control means activates the beam at a frequency of between 0.5 and 5 Hertz.

3. The radiographic apparatus according to claim 1 in which the control means activates the beam at a frequency of between 1 and 3 Hertz.

4. The radiographic apparatus according to claim 1 in which the control means activates the beam at a frequency that is between 6 and 10 times the frequency of the cyclical variation.

5. The radiographic apparatus according to claim 1 in which the selected point of the cycle is an extremity thereof.

6. The radiographic apparatus according to claim 1 in which the object is a patient.

7. The radiographic apparatus according to claim 6 in which the cyclical variation is the patient's breathing cycle.

8. The radiographic apparatus according to claim 2 in which the selected point of the cycle is an extremity thereof.

9. The radiographic apparatus according to claim 3 in which the selected point of the cycle is an extremity thereof.

10. The radiographic apparatus according to claim 4 in which the selected point of the cycle is an extremity thereof.

11. The radiographic apparatus according to claim 2 in which the object is a patient.

12. The radiographic apparatus according to claim 3 in which the object is a patient.

13. The radiographic apparatus according to claim 4 in which the object is a patient.

14. The radiographic apparatus according to claim 5 in which the object is a patient.

15. The radiographic apparatus according to claim 11 in which the cyclical variation is the patient's breathing cycle.

16. The radiographic apparatus according to claim 12 in which the cyclical variation is the patient's breathing cycle.

17. The radiographic apparatus according to claim 13 in which the cyclical variation is the patient's breathing cycle.

18. The radiographic apparatus according to claim 14 in which the cyclical variation is the patient's breathing cycle.

* * * * *

UNITED STATES PATENT AND TRADEMARK OFFICE
CERTIFICATE OF CORRECTION

| | | |
|---|---|---|
| PATENT NO. | : 7,924,971 B2 | Page 1 of 1 |
| APPLICATION NO. | : 12/445203 | |
| DATED | : April 12, 2011 | |
| INVENTOR(S) | : Knox et al. | |

It is certified that error appears in the above-identified patent and that said Letters Patent is hereby corrected as shown below:

Column 4, line 47, delete "11" and insert --12--.

Column 4, line 49, delete "12" and insert --13--.

Column 4, line 51, delete "13" and insert --14--.

Column 4, line 53, delete "14" and insert --15--.

Signed and Sealed this
Twentieth Day of March, 2012

David J. Kappos
*Director of the United States Patent and Trademark Office*